US009777307B2

(12) United States Patent
Feldman et al.

(10) Patent No.: US 9,777,307 B2
(45) Date of Patent: *Oct. 3, 2017

(54) HETEROCYCLIC NITROGEN CONTAINING POLYMER COATED ANALYTE MONITORING DEVICE AND METHODS OF USE

(71) Applicant: Abbott Diabetes Care Inc., Alameda, CA (US)

(72) Inventors: Benjamin J. Feldman, Berkeley, CA (US); Tianmei Ouyang, Fremont, CA (US); Hyun Cho, Berkeley, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/347,603

(22) Filed: Nov. 9, 2016

(65) Prior Publication Data
US 2017/0114384 A1    Apr. 27, 2017

Related U.S. Application Data

(63) Continuation of application No. 14/806,405, filed on Jul. 22, 2015, now Pat. No. 9,494,545, which is a
(Continued)

(51) Int. Cl.
*G01N 27/327* (2006.01)
*G01N 27/333* (2006.01)
(Continued)

(52) U.S. Cl.
CPC ............ *C12Q 1/006* (2013.01); *A61B 5/1495* (2013.01); *A61B 5/14532* (2013.01);
(Continued)

(58) Field of Classification Search
CPC ............ A61B 5/14532; A61B 5/14865; A61B 5/1495; C12C 1/001; C12C 1/006;
(Continued)

(56) References Cited

U.S. PATENT DOCUMENTS 5,262,305 A    11/1993  Heller et al.
5,264,104 A    11/1993  Gregg et al.
(Continued)

FOREIGN PATENT DOCUMENTS

WO    WO 2007120442    10/2007

OTHER PUBLICATIONS

Database WPI, Week 197723, Thomson Scientific, London, GB; AN 1977-40587Y & JP 52 051881 (Apr. 26, 1977).

*Primary Examiner* — Gurpreet Kaur
(74) *Attorney, Agent, or Firm* — Edward J. Baba; Khin K. Chin; Bozicevic, Field & Francis LLP

(57) ABSTRACT

The present invention is directed to membranes composed of heterocyclic nitrogen groups, such as vinylpyridine and to electrochemical sensors equipped with such membranes. The membranes are useful in limiting the diffusion of an analyte to a working electrode in an electrochemical sensor so that the sensor does not saturate and/or remains linearly responsive over a large range of analyte concentrations. Electrochemical sensors equipped with membranes described herein demonstrate considerable sensitivity and stability, and a large signal-to-noise ratio, in a variety of conditions.

18 Claims, 7 Drawing Sheets

Related U.S. Application Data continuation of application No. 14/463,453, filed on Aug. 19, 2014, now Pat. No. 9,096,881, which is a continuation of application No. 11/701,138, filed on Jan. 31, 2007, now Pat. No. 8,808,515.

(51) Int. Cl.

| | | |
|---|---|---|
| *C12Q 1/00* | (2006.01) | |
| *A61B 5/1486* | (2006.01) | |
| *A61B 5/145* | (2006.01) | |
| *A61B 5/1495* | (2006.01) | |

(52) U.S. Cl.
CPC ..... *A61B 5/14865* (2013.01); *G01N 27/3272* (2013.01); *G01N 27/3335* (2013.01)

(58) Field of Classification Search
CPC ............... A61K 38/28; G01N 27/3271; G01N 27/3335; G01N 27/3272
See application file for complete search history.

(56) References Cited

U.S. PATENT DOCUMENTS

| | | |
|---|---|---|
| 5,320,725 A | 6/1994 | Gregg et al. |
| 5,356,786 A | 10/1994 | Heller et al. |
| 5,593,852 A | 1/1997 | Heller et al. |
| 5,665,222 A | 9/1997 | Heller et al. |
| 5,972,199 A | 10/1999 | Heller et al. |
| 6,103,033 A | 8/2000 | Say et al. |
| 6,120,676 A | 9/2000 | Heller et al. |
| 6,134,461 A | 10/2000 | Say et al. |
| 6,143,164 A | 11/2000 | Heller et al. |
| 6,175,752 B1 | 1/2001 | Say et al. |
| 6,284,478 B1 | 9/2001 | Heller et al. |
| 6,329,161 B1 | 12/2001 | Heller et al. |
| 6,338,790 B1 | 1/2002 | Feldman et al. |
| 6,565,509 B1 | 5/2003 | Say et al. |
| 6,746,582 B2 | 6/2004 | Heller et al. |
| 6,932,894 B2 | 8/2005 | Mao et al. |
| 8,808,515 B2 * | 8/2014 | Feldman ............ A61B 5/14532 204/403.01 |
| 9,494,545 B2 * | 11/2016 | Feldman ............ A61B 5/14532 |
| 2003/0042137 A1 | 3/2003 | Mao et al. |
| 2005/0239154 A1 | 10/2005 | Feldman et al. |
| 2005/0241957 A1 | 11/2005 | Mao et al. |

* cited by examiner

HETEROCYCLIC NITROGEN CONTAINING POLYMER COATED ANALYTE MONITORING DEVICE AND METHODS OF USE

CROSS-REFERENCE TO RELATED APPLICATIONS

This application is a continuation of U.S. patent application Ser. No. 14/806,405, filed Jul. 22, 2015, issued as U.S. Pat. No. 9,494,545, which is a continuation of U.S. Pat. application Ser. No. 14/463,453, filed Aug. 19, 2014, issued as U.S. Pat. No. 9,096,881, which is a continuation of U.S. patent application Ser. No. 11/701,138, filed Jan. 31, 2007, issued as U.S. Pat. No. 8,808,515, the disclosures of which are incorporated herein by reference.

BACKGROUND OF THE INVENTION

Enzyme-based biosensors are devices in which an analyte-concentration-dependent biochemical reaction signal is converted into a measurable physical signal, such as an optical or electrical signal. Such biosensors are widely used in the detection of analytes in clinical, environmental, agricultural and biotechnological applications. Analytes that can be measured in clinical assays of fluids of the human body include, for example, glucose, lactate, cholesterol, bilirubin and amino acids. The detection of analytes in biological fluids, such as blood, is important in the diagnosis and the monitoring of many diseases.

Biosensors that detect analytes via electrical signals, such as current (amperometric biosensors) or charge (coulometric biosensors), are of special interest because electron transfer is involved in the biochemical reactions of many important bioanalytes. For example, the reaction of glucose with glucose oxidase involves electron transfer from glucose to the enzyme to produce gluconolactone and reduced enzyme. In an example of an amperometric glucose biosensor, glucose is oxidized by oxygen in the body fluid via a glucose oxidase-catalyzed reaction that generates gluconolactone and hydrogen peroxide, then the hydrogen peroxide is electrooxidized and correlated to the concentration of glucose in the body fluid.

Some biosensors are designed for implantation in a living animal body, such as a mammalian or a human body, merely by way of example. In an implantable amperometric biosensor, the working electrode is typically constructed of a sensing layer, which is in direct contact with the conductive material of the electrode, and a diffusion-limiting membrane layer on top of the sensing layer. The sensing layer typically consists of an enzyme, an optional enzyme stabilizer such as bovine serum albumin (BSA), and a crosslinker that cross-links the sensing layer components. Alternatively, the sensing layer consists of an enzyme, a polymeric redox mediator, and a crosslinker that crosslinks the sensing layer components, as is the case in—"wired-enzyme" biosensors.

In an implantable amperometric glucose sensor, the membrane is often beneficial or necessary for regulating or limiting the flux of glucose to the sensing layer. By way of explanation, in a glucose sensor without a membrane, the flux of glucose to the sensing layer increases linearly with the concentration of glucose. When all of the glucose arriving at the sensing layer is consumed, the measured output signal is linearly proportional to the flux of glucose and thus to the concentration of glucose. However, when the glucose consumption is limited by the rate of one or more of the chemical or electrochemical reactions in the sensing layer, the measured output signal is no longer controlled by the flux of glucose and is no longer linearly proportional to the flux or concentration of glucose. In this case, only a fraction of the glucose arriving at the sensing layer is contributing to the current. The current no longer increases linearly with the glucose concentration but becomes saturated, meaning that it increases less and less for a given increment of glucose concentration, and eventually stops increasing with the concentration of glucose. In a glucose sensor equipped with a diffusion-limiting membrane, on the other hand, the membrane reduces the flux of glucose to the sensing layer such that the sensor does not become saturated, or becomes saturated only at much higher glucose concentrations and can therefore operate effectively resolve an increase in the concentration of glucose when the glucose concentration is high.

There have been various attempts to develop glucose-diffusion-limiting membranes. The membranes were, however, usually made of polymers, and either their average thickness and/or the microscopic uniformity of their thickness was difficult to control and/or reproduce. As a result, the glucose fluxes through the membranes, which determined the sensitivities of the glucose sensors employing such membranes were widely scattered, indicative of lack of adequate control in the membrane-making process. Thus, there is a need for a glucose-diffusion-limiting membrane that provides adequate regulation of the flux of glucose to the sensing layer and that is mechanically strong, biocompatible, and easily and reproducibly manufactured.

In an implantable amperometric glucose or other analyte sensor, the membrane can be also beneficial or necessary for regulating or limiting the flux of an interferant to the sensing layer, the interferant affecting the signal, for example the current produced by the analyte. By affecting the signal, the interferant adds to the measurement's error. The preferred membranes reduce the flux of the interferant more than they reduce the flux of the analyte, for example of glucose.

SUMMARY OF THE INVENTION

The present application is directed to membranes composed of heterocyclic nitrogen groups, such as vinylpyridine and to electrochemical sensors equipped with such membranes. The membranes are useful in limiting the diffusion of an analyte to a working electrode in an electrochemical sensor so that the sensor does not saturate and/or remains linearly responsive over a large range of analyte concentrations. Electrochemical sensors equipped with membranes described herein demonstrate considerable sensitivity and stability, and a large signal-to-noise ratio, in a variety of conditions.

Described herein is an electrochemical sensor, including a working electrode having a sensing layer in contact with a conductive material of the electrode; a membrane disposed over the sensing layer, wherein the membrane comprises a crosslinker and a polymer having the formula:

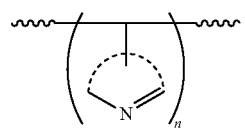

wherein the solid horizontal line represents a polymer backbone and n is a positive integer; and a counter electrode in electrochemical communication with the working electrode.

In some embodiments, the sensing layer of the working electrode includes a glucose-responsive enzyme. In some embodiments, the sensing layer of the working electrode comprises a redox mediator. In certain embodiments, the redox mediator includes a complex selected from the group consisting of a ruthenium-containing complex and an osmium-containing complex. In certain embodiments, the redox mediator is non-leachable with respect to the working electrode. In certain embodiments, the redox mediator is immobilized on the working electrode.

In some embodiments, the polymer comprises the formula:

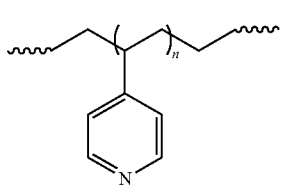

wherein n is a positive integer. In some embodiments, the crosslinker comprises a poly(ethylene glycol). In certain embodiments, the poly(ethylene glycol) is a poly(ethylene glycol) diglycidyl ether. In some embodiments, the membrane limits flux of glucose or lactate thereacross. In some embodiments, the membrane limits flux of glucose or lactose thereacross in vivo.

Also described herein is an electrode for use in a biosensor, including a sensing layer in contact with a conductive material of the electrode, and a membrane disposed over the sensing layer, wherein the membrane comprises a crosslinker and a polymer having the formula:

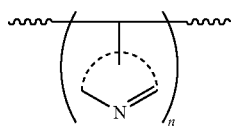

wherein the solid horizontal line represents a polymer backbone and n is a positive integer.

In some embodiments, the sensing layer of the working electrode includes a glucose-responsive enzyme. In some embodiments, the sensing layer of the working electrode comprises a redox mediator. In certain embodiments, the redox mediator includes a complex selected from the group consisting of a ruthenium-containing complex and an osmium-containing complex. In certain embodiments, the redox mediator is non-leachable with respect to the working electrode. In certain embodiments, the redox mediator is immobilized on the working electrode. In some embodiments, the polymer comprises the formula:

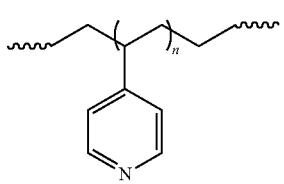

wherein n is a positive integer. In some embodiments, the crosslinker comprises a poly(ethylene glycol). In certain embodiments, the poly(ethylene glycol) is a poly(ethylene glycol) diglycidyl ether. In some embodiments, the membrane limits flux of glucose or lactate thereacross. In some embodiments, the membrane limits flux of glucose or lactose thereacross in vivo.

Also described herein is an analyte sensor assembly, including an electrochemical sensor having a flexible substrate comprising (i) at least one working electrode comprising a sensing layer and a membrane disposed over the sensing layer, wherein the membrane comprises a crosslinker and a polymer having the formula:

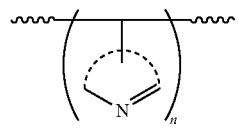

wherein the solid horizontal line represents a polymer backbone and n is a positive integer, (ii) at least one counter electrode, and (iii) at least one contact pad coupled to each of the working and counter electrodes, wherein the electrochemical sensor is adapted for implantation of a portion of the electrochemical sensor comprising the working and counter electrodes through skin; and an electrochemical sensor control unit comprising (i) a housing adapted for placement on skin; (ii) a plurality of conductive contacts disposed on the housing and configured for coupling to the contact pads of the electrochemical sensor; and (iii) an rf transmitter disposed in the housing and coupled to the plurality of conductive contacts for transmitting data obtained using the electrochemical sensor.

In some embodiments, the sensing layer of the working electrode includes a glucose-responsive enzyme. In some embodiments, the sensing layer of the working electrode comprises a redox mediator. In certain embodiments, the redox mediator includes a complex selected from the group consisting of a ruthenium-containing complex and an osmium-containing complex. In certain embodiments, the redox mediator is non-leachable with respect to the working electrode. In certain embodiments, the redox mediator is immobilized on the working electrode. In some embodiments, the polymer comprises the formula:

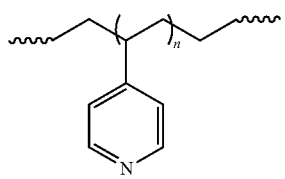

wherein n is a positive integer. In some embodiments, the crosslinker comprises a poly(ethylene glycol). In certain embodiments, the poly(ethylene glycol) is a poly(ethylene glycol) diglycidyl ether. In some embodiments, the membrane limits flux of glucose or lactate thereacross. In some embodiments, the membrane limits flux of glucose or lactose thereacross in vivo.

Also described herein is a method for monitoring a level of an analyte using the analyte monitoring system including, inserting the electrochemical sensor into skin of a patient; attaching the electrochemical sensor control unit to the skin of the patient; coupling a plurality of conductive contacts disposed in the sensor control unit to a plurality of contact pads disposed on the sensor; collecting data, using the sensor control unit, regarding a level of an analyte from signals generated by the sensor; transmitting the collected data to the display unit using the rf transmitter of the sensor control unit; and displaying an indication of the level of the analyte on the display of the display unit.

In some embodiments, the analyte is glucose. In some embodiments, the polymer comprises the formula:

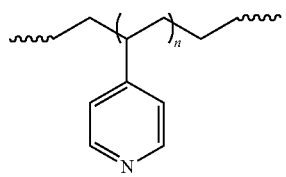

wherein n is a positive integer. In some embodiments, the crosslinker comprises a poly(ethylene glycol). In certain embodiments, the poly(ethylene glycol) is a poly(ethylene glycol) diglycidyl ether. In some embodiments, the collecting data includes generating signals from the sensor and processing the signals into data. In some embodiments, the data includes the signals from the sensor. In certain embodiments, the method further includes activating an alarm if the data indicates an alarm condition. In certain embodiments, the method further includes administering a drug, such as insulin, in response to the data. In some embodiments, the method further includes obtaining a calibration value from a calibration device to calibrate the data. In some embodiments, the calibration device is coupled to the display unit. In some embodiments, the method further includes transmitting the calibration, value from a transmitter in the display unit to a receiver in the sensor control unit.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

Figure 1:
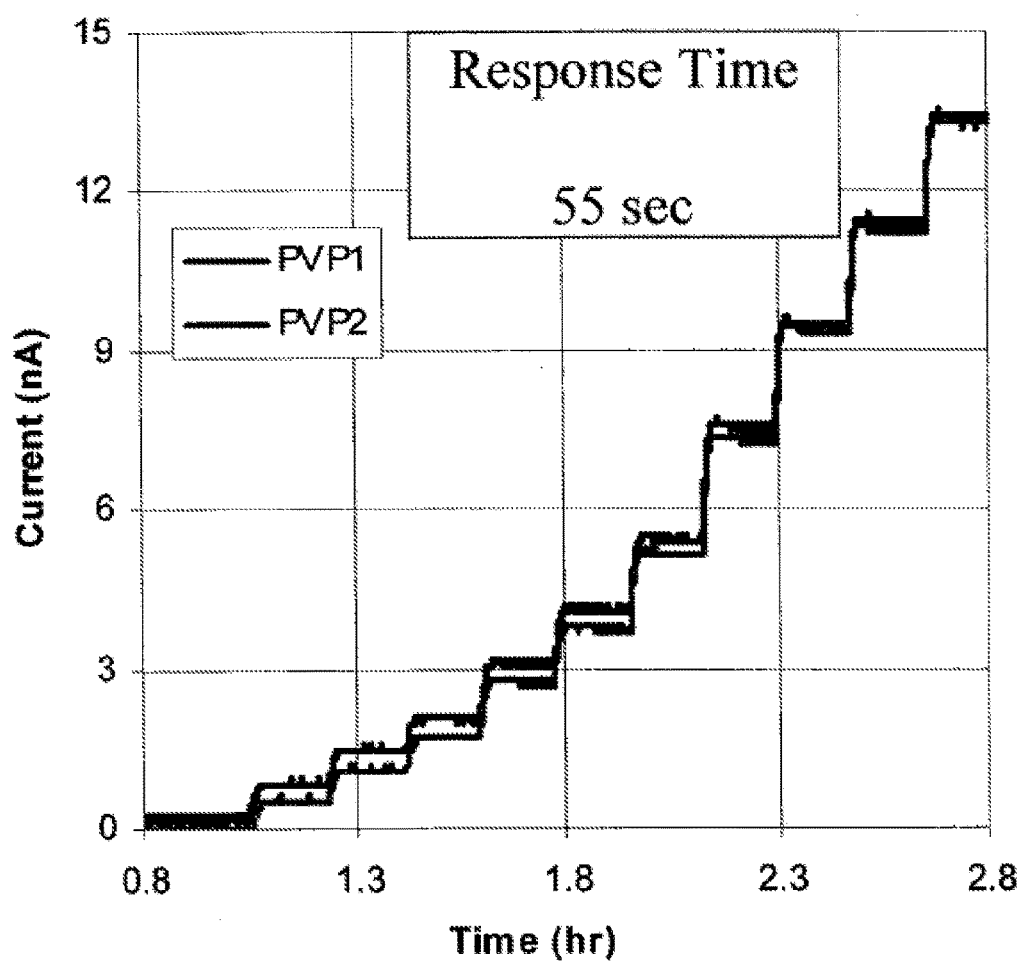
FIG. 1 is a calibration curve for two sensors (PVP1 and PVP2) having diffusion-limiting membranes described herein were tested simultaneously, both at 37° C. The sensors were placed in a PBS-buffered solution (pH 7) and the output current of each of the sensors was measured over time.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the compound" includes reference to one or more compounds and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present application is directed to membranes composed of vinylpyridine groups and to electrochemical sensors equipped with such membranes. The membranes are useful in limiting the diffusion of an analyte to a working electrode in an electrochemical sensor so that the sensor does not saturate and/or remains linearly responsive over a large range of analyte concentrations. Electrochemical sensors equipped with membranes described herein demonstrate considerable sensitivity and stability, and a large signal-to-noise ratio, in a variety of conditions.

In general, a membrane described herein is formed by crosslinking a modified polymer containing heterocyclic nitrogen groups in an alcohol-buffer mixed solvent and allowing the membrane solution to cure over time. The resulting membrane is capable of limiting the flux of an analyte from one space, such as a space associated with a biofluid, to another space, such as space associated with an enzyme-containing sensing layer. A "biological fluid" or "biofluid" is any body fluid or body fluid derivative in which the analyte can be measured, for example, blood, interstitial fluid, plasma, dermal fluid, sweat, and tears. An amperometric glucose sensor constructed of a wired-enzyme sensing layer and a glucose-diffusion-limiting layer described herein is very stable and has a large linear detection range.

Diffusion Limiting Membranes

The diffusion limiting membranes include polymers having heterocyclic nitrogen groups and have the following general formula I:

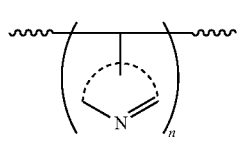

wherein the horizontal line represents a polymer backbone and n is a positive integer from about 150 to about 15,000, including about 500 to about 12,000, about 750 to about 10,000, about 1,000 to about 9,000, such as about 1,500, 2,000, 2,500, 5,000, 7,000, etc. The term "heterocyclic nitrogen group" refers to a cyclic structure containing a nitrogen in a ring of the structure.

In certain embodiments, the polymer backbone further includes a copolymer component, referred to herein as "D". Examples of copolymer components include, but are not limited to, phenylalkyl, alkoxystyrene, hydroxyalkyl, alkoxyalkyl, alkoxycarbonylalkyl, and a molecule containing a poly(ethylene glycol) or polyhydroxyl group. Some poly(heterocyclic nitrogen-co-D) polymers suitable as starting materials are commercially available. For example, poly(2-vinylpyridine-co-styrene), poly(4-vinylpyridine-co-styrene) and poly(4-vinylpyridine-co-butyl methacrylate) are available from Aldrich Chemical Company, Inc. Other poly(heterocyclic nitrogen-co-D) polymers can be readily synthesized by anyone skilled in the art of polymer chemistry using well-known methods. For example, D is a styrene or a C1-C18 alkyl methacrylate component of a polyvinylpyridine-poly-D, such as (4-vinylpyrine-co-styrene) or poly(4-vinylpyridine-co-butyl methacrylate). D may contribute to various desirable properties of the membrane including, but not limited to, hydrophobicity, hydrophilicity, solubility, biocompatibility, elasticity and strength. D may be selected to optimize or "fine-tune" a membrane made from the polymer in terms of its permeability to an analyte and its non-permeability to an undesirable, interfering component, for example.

The heterocyclic nitrogen groups of Formula I include, but are not limited to, pyridine, imidazole, oxazole, thiazole, pyrazole, or any derivative thereof. In some embodiments, the heterocyclic nitrogen groups are vinylpyridine, such as 2-, 3-, or 4-vinylpyridine, or vinylimidazole, such as 1-, 2-, or 4-vinylimidazole. In certain embodiments, the heterocyclic nitrogen groups are 4-vinylpyridine, such that the polymer is a derivative of poly(4-vinylpyridine). The terms "polyvinylpyridine" or "PVP" refer to poly(4-vinylpyridine), poly(3-vinylpyridine), or poly(2-vinylpyridine), as well as any copolymer of vinylpyridine and a second or a third copolymer component. An example of such a poly(4-vinylpyridine) membrane has the following general formula, Formula II:

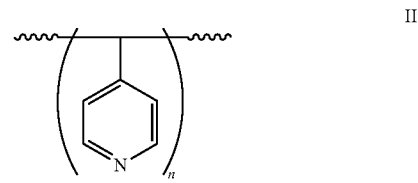

wherein the horizontal line represents a polymer backbone and n is a positive integer. A further example of such a poly(4-vinylpyridine) membrane has the following general formula, Formula III

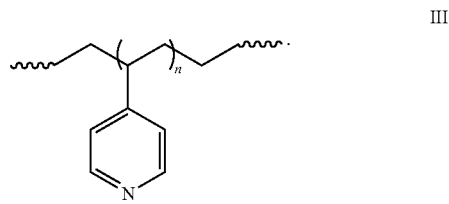

wherein n is a positive integer.

In some embodiments, the membranes further include a crosslinking agent. A "crosslinker" is a molecule that contains at least two reactive groups capable of linking at least two molecules together, or linking at least two portions of the same molecule together. Linking of at least two molecules is called intermolecular crosslinking, while linking of at least two portions of the same molecule is called intramolecular crosslinking. A crosslinker having more than two reactive groups may be capable of both intermolecular and intramolecular crosslinkings at the same time. A "reactive group" is a functional group of a molecule that is capable of reacting with another compound to couple at least a portion of that other compound to the molecule. Reactive groups include carboxy, activated ester, sulfonyl halide, sulfonate ester, isocyanate, isothiocyanate, epoxide, aziridine, halide, aldehyde, ketone, amine, acrylamide, thiol, acyl azide, acyl halide, hydrazine, hydroxylamine, alkyl halide, imidazole, pyridine, phenol, alkyl sulfonate, halotriazine, imido ester, maleimide, hydrazide, hydroxy, and photo-reactive azido aryl groups. Activated esters, as understood in the art, generally include esters of succinimidyl, benzotriazolyl, or aryl substituted by electron-withdrawing groups such as sulfo, nitro, cyano, or halo groups; or carboxylic acids activated by carbodiimides.

Crosslinkers suitable for use with the membranes include molecules having at least two reactive groups, such as bi-, tri-, or tetra-functional groups, capable of reacting with the heterocyclic nitrogen groups, such as the pyridine groups, of the polymer. Suitable crosslinkers include, but are not limited to, derivatives of poly(ethylene glycol) or poly(propylene glycol), epoxide (glycidyl group), aziridine, alkyl halide, and sulfonate esters. Alkylating groups of the crosslinkers are preferably glycidyl groups. Preferably, glycidyl crosslinkers have a molecular weight of from about 200 to about 4,000 and are water soluble or soluble in a water-miscible solvent, such as an alcohol. Examples of suitable crosslinkers include, but are not limited to, poly(ethylene glycol) diglycidyl ether with a molecular weight of about 250 to about 2000, including about 350 to about 150, such as about 650. An exemplary crosslinker has the following general formula, Formula IV:

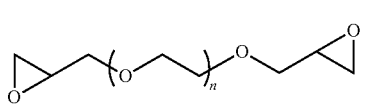

IV wherein n is a positive integer, such as from about 1 to about 15, including about 8, 9, 10, 11, etc.

In certain embodiments, it is desirable to have a slow crosslinking reaction during the dispensing of membrane solution so that the membrane coating solution has a reasonable pot-life for large-scale manufacture. A fast crosslinking reaction results in a coating solution of rapidly changing viscosity, which renders coating difficult. For example, the crosslinking reaction is slow during the dispensing of the membrane solution, and accelerated during the curing of the membrane at ambient temperature, or at an elevated temperature where possible.

An example of a process for producing a membrane is now described. For example, the polymer and a suitable crosslinker are dissolved in a buffer-containing solvent, typically a buffer-alcohol mixed solvent, to produce a membrane solution. In some embodiments, the buffer has a pH of about 7.5 to about 9.5 and the alcohol is ethanol. For example, the buffer is a 10 mM (2-(4-(2-hydroxyethyl)-1-piperazine)ethanesulfonate) (HEPES) buffer (pH 8) and the ethanol to buffer volume ratio is from about 95 to 5 to about 0 to 100. A minimum amount of buffer is necessary for the crosslinking chemistry. The amount of solvent needed to dissolve the polymer and the crosslinker may vary depending on the nature of the polymer and the crosslinker. For example, a higher percentage of alcohol may be required to dissolve a relatively hydrophobic polymer and/or crosslinker.

The ratio of polymer to cross-linker is important to the nature of the final membrane. By way of example, if an inadequate amount of crosslinker or an extremely large excess of crosslinker is used, crosslinking is insufficient and the membrane is weak. Further, if a more than adequate amount of crosslinker is used, the membrane is overly crosslinked such that membrane is too brittle and/or impedes analyte diffusion. Thus, there is an optimal ratio of a given polymer to a given crosslinker that should be used to prepare a desirable or useful membrane. By way of example, the optimal polymer to crosslinker ratio by weight is typically from about 4:1 to about 32:1 for a polymer of any of Formulas I to III above and a poly(ethylene glycol) diglycidyl ether crosslinker, having a molecular weight of about 200 to about 400. For example, this range is from about 2:1 to about 25:1, including about 3:1 to about 22:1, about 4:1 to about 20:1, about 5:1 to about 16:1, etc. Further by way of example, the optimal polymer to crosslinker ratio by weight is typically about 10:1 for a polymer of Formula III above and a poly(ethylene glycol) diglycidyl ether crosslinker having a molecular weight of about 650.

The membrane solution can be coated over a variety of biosensors that may benefit from having a membrane disposed over the enzyme-containing sensing layer. A "sensing layer" is a component of the sensor which includes constituents that facilitate the electrolysis of the analyte. The sensing layer may include constituents such as an electron transfer agent, a catalyst which catalyzes a reaction of the analyte to produce a response at the electrode, or both. In some embodiments of the sensor, the sensing layer is non-leachably disposed in proximity to or on the working electrode. A "non-leachable" or "non-releasable" compound or a compound that is "non-leachably disposed" is meant to define a compound that is affixed on the sensor such that it does not substantially diffuse away from the working surface of the working electrode for the period in which the sensor is used (e.g., the period in which the sensor is implanted in a patient or measuring a sample). A "working surface" is that portion of the working electrode which is coated with or is accessible to the electron transfer agent and configured for exposure to an analyte-containing fluid.

In some embodiments, the sending layer further includes a redox mediator. A "redox mediator" is an electron-transfer agent for carrying electrons in one or more of the steps of the signal producing reaction or the reactions, for example between an analyte, an analyte-reduced or analyte-oxidized enzyme, and an electrode, either directly, or via one or more additional electron-transfer agents. A redox mediator that includes a polymeric backbone may also be referred to as a "redox polymer". Examples of redox mediators include ruthenium-containing complexes and osmium-containing complexes.

Examples of such biosensors include, but are not limited to, glucose sensors and lactate sensors. (See U.S. Pat. No. 6,134,461 to Heller et al., which is incorporated herein in its entirety by this reference.) The coating process may comprise any commonly used technique, such as spin-coating, dip-coating, doctor blading or dispensing droplets of the membrane solution over the sensing layers, and the like, followed by curing under ambient conditions typically for 1 to 2 days. The particular details of the coating process (such as dip duration, dip frequency, number of dips, or the like) may vary.

Sensor fabrication typically includes depositing an enzyme-containing sensing layer over a working electrode and casting the diffusion-limiting membrane layer over the sensing layer, and optionally, but preferably, also over the counter and reference electrodes. Sensors having other configurations such as a three-electrode design can also be prepared using similar methods.

Electrochemical Sensors

An electrochemical sensor that includes at least one working electrode with membranes including heterocyclic nitrogen groups, such as polyvinylpyridine, disposed thereon can be formed on a substrate. The sensor may also include at least one counter electrode (or counter/reference electrode) and/or at least one reference electrode. An "electrochemical sensor" is a device configured to detect the presence and/or measure the level of an analyte in a sample, via an electrochemical oxidation or reduction reaction on the sensor, or via a sequence of chemical reactions where at least one of the chemical reactions is an electrochemical oxidation or reduction reactions on the sensor. These reactions are transduced to an electrical signal that can be correlated to an amount, concentration, or level of an analyte in the sample.

A "working electrode" is an electrode at which the analyte, or a compound whose level depends on the level of the analyte, is electrooxidized or electroreduced with or without the agency of an electron transfer agent. A "counter electrode" refers to an electrode paired with the working electrode, through which passes a current about equal in magnitude and opposite in sign to the current passing through the working electrode. In the context of the invention, the term "counter electrode" is meant to include counter electrodes which also function as reference electrodes (i.e., a counter/reference electrode). The term "reference electrode" includes both a) reference electrodes and b) reference electrodes that also function as counter electrodes (i.e., counter/reference electrodes), unless otherwise indicated. The term "counter electrode" includes both a) counter electrodes and b) counter electrodes that also function as reference electrodes (i.e., counter/reference electrodes), unless otherwise indicated.

The counter electrode and/or reference electrode may be formed on the substrate or may be separate. For example, the counter electrode and/or reference electrode may be formed on a second substrate which is also implanted in the patient or, for some embodiments of the implantable sensors, the counter electrode and/or reference electrode may be placed on the skin of the patient with the working electrode or electrodes being implanted into the patient. The use of an on-the-skin counter and/or reference electrode with an implantable working electrode is described in U.S. Pat. No. 5,593,852.

The working electrode or electrodes are formed using conductive traces disposed on the substrate. The counter electrode and/or reference electrode, as well as other optional portions of the sensor, such as a temperature probe, may also be formed using conductive traces disposed on the substrate. These conductive traces may be formed over a smooth surface of the substrate or within channels formed by, for example, embossing, indenting or otherwise creating a depression in the substrate.

The sensing layer is often formed proximate to or on at least one of the working electrodes to facilitate the electrochemical detection of the analyte and the determination of its level in the sample fluid, particularly if the analyte can not be electrolyzed at a desired rate and/or with a desired specificity on a bare electrode. The sensing layer may include an electron transfer agent to transfer electrons directly or indirectly between the analyte and the working electrode. An "electron transfer agent" is a compound that carries electrons between the analyte and the working electrode, either directly, or in cooperation with other electron transfer agents. One example of an electron transfer agent is a redox mediator.

The sensing layer may also contain a catalyst to catalyze a reaction of the analyte. The components of the sensing layer may be in a fluid or gel that is proximate to or in contact with the working electrode. Alternatively, the components of the sensing layer may be disposed in a polymeric or sol-gel matrix that is proximate to or on the working electrode. In general, the components of the sensing layer are non-leachably disposed within the sensor. For example, the components of the sensor are immobilized within the sensor. In addition to the electrodes and the sensing layer, the sensor may also include a temperature probe, a biocompatible layer, and/or other optional components. A compound is "immobilized" on a surface when it is entrapped on or chemically bound to the surface. Components are "immobilized" within a sensor, for example, when the components are covalently, ionically, or coordinatively bound to constituents of the sensor and/or are entrapped in a polymeric or sol-gel matrix or membrane which precludes their loss by out-diffusion.

For example, a glucose or lactate sensor may include a first sensing layer which is spaced apart from the working electrode and contains an enzyme, for example, glucose oxidase or lactate oxidase. The reaction of glucose or lactate in the presence of the appropriate enzyme forms hydrogen peroxide. A second sensing layer is provided directly on the working electrode and contains a peroxidase enzyme and an electron transfer agent to generate a signal at the electrode in response to the hydrogen peroxide. The level of hydrogen peroxide indicated by the sensor then correlates to the level of glucose or lactate. Another sensor which operates similarly can be made using a single sensing layer with both the glucose or lactate oxidase and the peroxidase being deposited in the single sensing layer. Examples of such sensors are described in U.S. Pat. No. 5,593,852, U.S. patent application Ser. No. 08/540,789, and PCT Patent Application No. US98/02403.

In some embodiments, one or more of the working electrodes do not have a corresponding sensing layer, or have a sensing layer which does not contain one or more components (e.g., an electron transfer agent or catalyst) needed to electrolyze the analyte. The signal generated at this working electrode typically arises from interferents and other sources, such as electrooxidizable or electroreducible ions, in the fluid, and not in response to the analyte (because the analyte is not electrooxidized or electroreduced). Thus, the signal at this working electrode adds to a background signal. The background signal can be subtracted from the analyte signal obtained from other working electrodes that are associated with fully-functional sensing layers.

The substrate may be formed using a variety of non-conducting materials, including, for example, polymeric or plastic materials and ceramic materials. Suitable materials for a particular sensor may be determined, at least in part, based on the desired use of the sensor and properties of the materials.

In some embodiments, the substrate is flexible. For example, if the sensor is configured for implantation into a patient, then the sensor may be made flexible (although rigid sensors may also be used for implantable sensors) to reduce pain to the patient and damage to the tissue caused by the implantation of and/or the wearing of the sensor. A flexible substrate often increases the patient's comfort and allows a wider range of activities. Suitable materials for a flexible substrate include, for example, non-conducting plastic or polymeric materials and other non-conducting, flexible, deformable materials. Examples of useful plastic or polymeric materials include thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate).

In other embodiments, the sensors are made using a relatively rigid substrate to, for example, provide structural support against bending or breaking. Examples of rigid materials that may be used as the substrate include poorly conducting ceramics, such as aluminum oxide and silicon dioxide. One advantage of an implantable sensor having a rigid substrate is that the sensor may have a sharp point and/or a sharp edge to aid in implantation of a sensor without an additional insertion device.

It will be appreciated that for many sensors and sensor applications, both rigid and flexible sensors will operate adequately. The flexibility of the sensor may also be controlled and varied along a continuum by changing, for example, the composition and/or thickness of the substrate.

In addition to considerations regarding flexibility, it is often desirable that implantable sensors should have a substrate which is physiologically harmless, for example, a substrate approved by a regulatory agency or private institution for in vivo use.

The sensor may include optional features to facilitate insertion of an implantable sensor. For example, the sensor may be pointed at the tip to ease insertion. In addition, the sensor may include a barb which assists in anchoring the sensor within the tissue of the patient during operation of the sensor. However, the barb is typically small enough so that little damage is caused to the subcutaneous tissue when the sensor is removed for replacement.

At least one conductive trace is formed on the substrate for use in constructing a working electrode. In addition, other conductive traces may be formed on the substrate for use as electrodes (e.g., additional working electrodes, as well as counter, counter/reference, and/or reference electrodes) and other components, such as a temperature probe. The conductive traces may extend most of the distance along a length of the sensor, although this is not necessary. The placement of the conductive traces may depend on the particular configuration of the analyte monitoring system (e.g., the placement of control unit contacts and/or the sample chamber in relation to the sensor). For implantable sensors, particularly subcutaneously implantable sensors, the conductive traces typically extend close to the tip of the sensor to minimize the amount of the sensor that must be implanted.

Typically, each of the conductive traces includes a contact pad. The contact pad may simply be a portion of the conductive trace that is indistinguishable from the rest of the trace except that the contact pad is brought into contact with the conductive contacts of a control unit (e.g., the sensor control unit). More commonly, however, the contact pad is a region of the conductive trace that has a larger width than other regions of the trace to facilitate a connection with the contacts on the control unit. By making the contact pads relatively large as compared with the width of the conductive traces, the need for precise registration between the contact pads and the contacts on the control unit is less critical than with small contact pads.

To electrolyze the analyte, a potential (versus a reference potential) is applied across the working and counter electrodes. The minimum magnitude of the applied potential is often dependent on the particular electron transfer agent, analyte (if the analyte is directly electrolyzed at the electrode), or second compound (if a second compound, such as oxygen or hydrogen peroxide, whose level is dependent on the analyte level, is directly electrolyzed at the electrode). The applied potential usually equals or is more oxidizing or reducing, depending on the desired electrochemical reaction, than the redox potential of the electron transfer agent, analyte, or second compound, whichever is directly electrolyzed at the electrode. The potential at the working electrode is typically large enough to drive the electrochemical reaction to or near completion.

When a potential is applied between the working electrode and the counter electrode, an electrical current will flow. The current is a result of the electrolysis of the analyte or a second compound whose level is affected by the analyte. "Electrolysis" is the electrooxidation or electroreduction of a compound either directly at an electrode or via one or more electron transfer agents. In one embodiment, the electrochemical reaction occurs via an electron transfer agent and the optional catalyst. Many analytes B are oxidized (or reduced) to products C by an electron transfer agent species A in the presence of an appropriate catalyst (e.g., an enzyme). The electron transfer agent A is then oxidized (or reduced) at the electrode. Electrons are collected by (or removed from) the electrode and the resulting current is measured.

As an example, an electrochemical sensor may be based on the reaction of a glucose molecule with two non-leachable ferricyanide anions in the presence of glucose oxidase to produce two non-leachable ferrocyanide anions, two hydrogen ions, and gluconolactone. The amount of glucose present is assayed by electrooxidizing the non-leachable ferrocyanide anions to non-leachable ferricyanide anions and measuring the current.

An implantable sensor may also, optionally, have an anticlotting agent disposed on a portion the substrate which is implanted into a patient. This anticlotting agent may reduce or eliminate the clotting of blood or other body fluid around the sensor, particularly after insertion of the sensor. Blood clots may foul the sensor or irreproducibly reduce the amount of analyte which diffuses into the sensor. Examples of useful anticlotting agents include heparin and tissue plasminogen activator (TPA), as well as other known anticlotting agents.

The anticlotting agent may be applied to at least a portion of that part of the sensor that is to be implanted. The anticlotting agent may be applied, for example, by bath, spraying, brushing, or dipping. The anticlotting agent is allowed to dry on the sensor. The anticlotting agent may be immobilized on the surface of the sensor or it may be allowed to diffuse away from the sensor surface. Typically, the quantities of anticlotting agent disposed on the sensor are far below the amounts typically used for treatment of medical conditions involving blood clots and, therefore, have only a limited, localized effect.

Figure 4A:
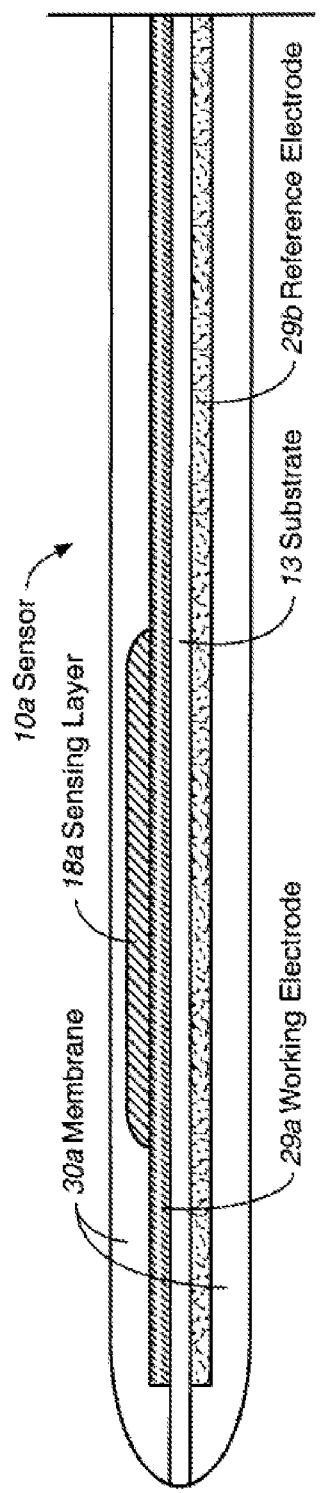
FIG. 4A is a is a schematic, side-view illustration of a portion of a two-electrode glucose sensor having a working electrode, a combined counter/reference electrode, and a dip-coated membrane that encapsulates both electrodes, according to the present invention.
Figure 4B:
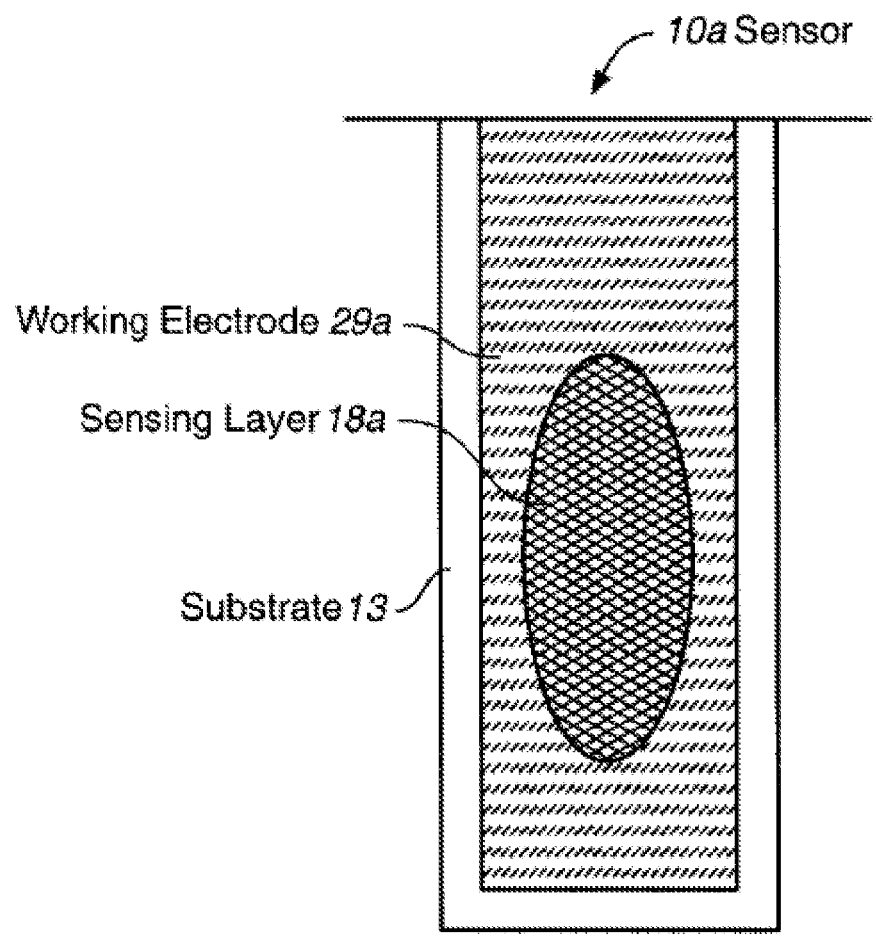
FIG. 4B is a schematic top-view illustration of the exemplary sensor of FIG. 4A.
Figure 4C:
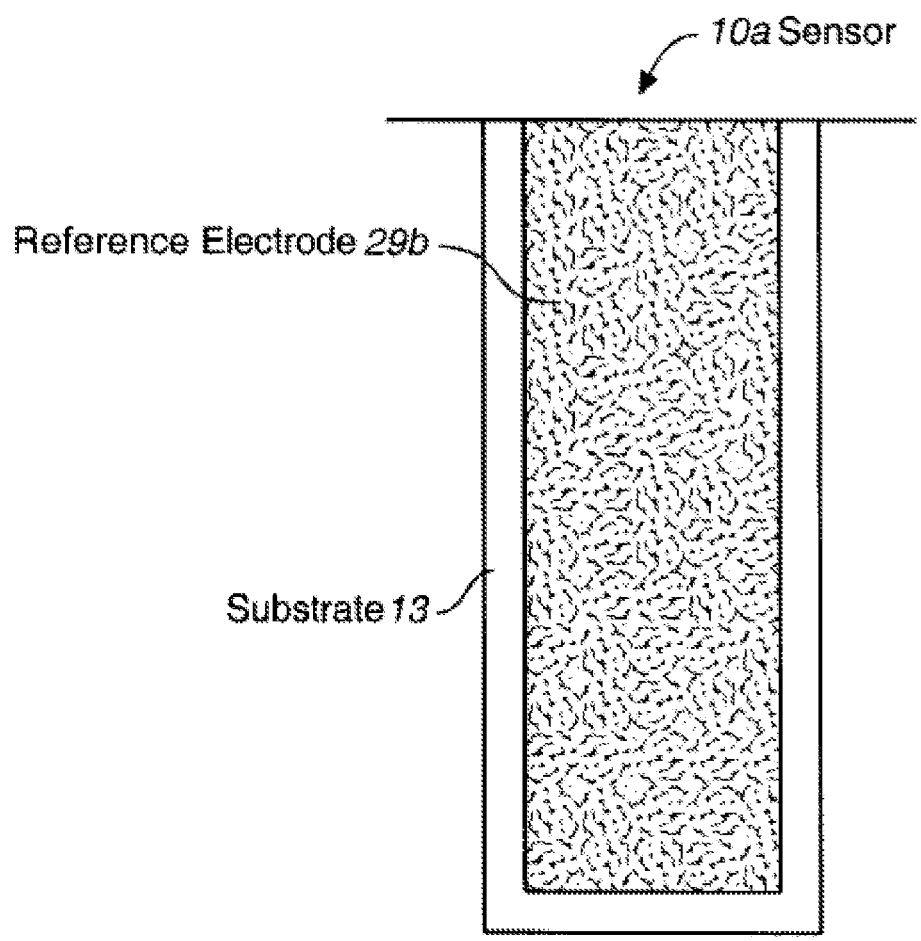
FIG. 4C is a schematic bottom-view illustration of the exemplary sensor of FIG. 4A.

By way of example, the membrane may be used in a two-electrode amperometric glucose sensor, as shown in FIGS. 4A-4C (collectively FIG. 4). The amperometric glucose sensor 10a of FIG. 4 includes a substrate 13 disposed between a working electrode 29a that is typically carbon-based, and an Ag/AgCl counter/reference electrode 29b. A sensor or sensing layer 18a is disposed on the working electrode. A membrane or membrane layer 30a encapsulates the entire glucose sensor 10a, including the Ag/AgCl counter/reference electrode. The sensing layer 18a of the glucose sensor 10a includes, for example, crosslinked glucose oxidase and a low potential polymeric osmium complex mediator, as disclosed in the above-mentioned Published PCT Application, International Publication No. WO 01/36660 A2. The enzyme- and mediator-containing formulation that can be used in the sensing layer, and methods for applying them to an electrode system, are known in the art, for example, from the above-mentioned U.S. Pat. No. 6,134,461 of Say et al.

Figure 5:
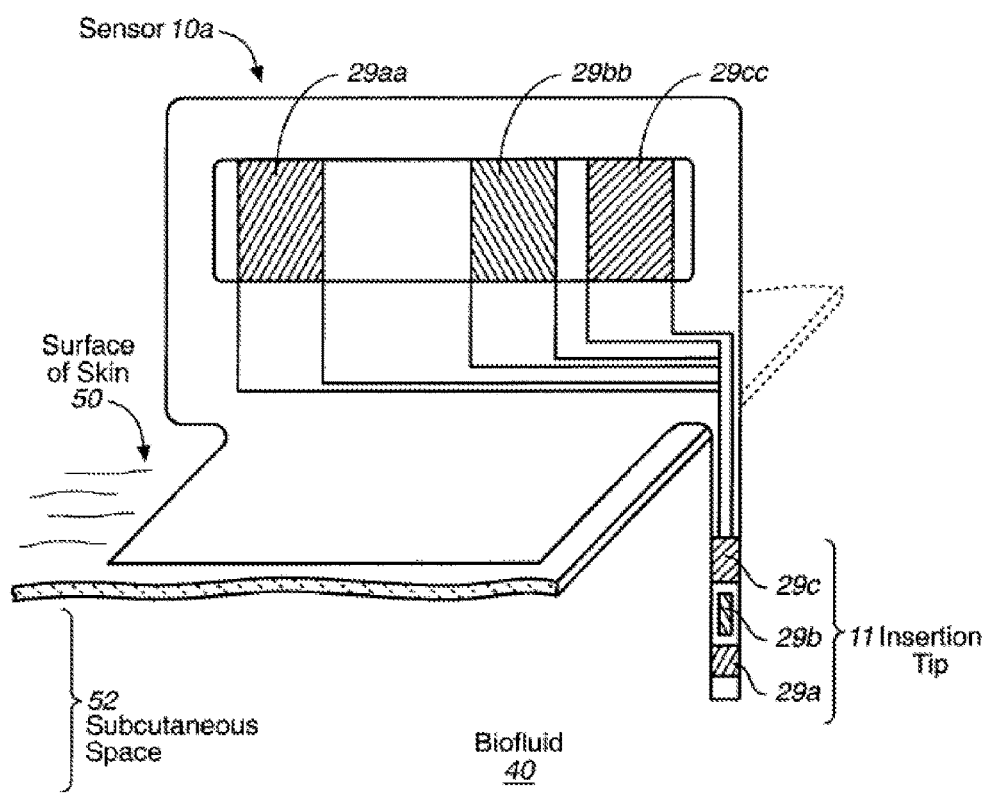
FIG. 5 is a schematic perspective view of a transcutaneous electrochemical sensor as it would be seen partially implanted into the skin Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

By way of example, the membrane may also be used in stacked electrode glucose sensor, as shown in FIG. 5. FIG. 5 illustrates a fully fabricated sensor, with a catalytic agent incorporated into a protective membrane, as the sensor would be seen placed on the skin, with a portion of the sensor transcutaneously inserted into the subcutaneous space. FIG. 5 provides a perspective view of a sensor 10*a*, the major portion of which is above the surface of the skin 50, with an insertion tip 11 penetrating through the skin and into the subcutaneous space 52, where it is bathed in biofluid 40. Contact portions of a working electrode 29*aa*, a reference electrode 29*bb*, and a counter electrode 29*cc* can be seen on the portion of the sensor 10*a* situated above the skin surface. Working electrode 29*a*, a reference electrode 29*b*, and a counter electrode 29*c* can be seen at the end of the insertion tip 11. As shown in FIG. 5 the electrodes are provided in a stacked configuration on the sensor insertion tip 11. The working electrode 29*a* is shown resting on top of a plastic substrate 13, a wired enzyme sensing layer 18*a* rests on top of a portion of the working electrode 29*a*. Overlaying the sensing layer and a portion of the electrode, depicted transparently, is an interfacing membrane 30*a*, and associated with and dispersed throughout the membrane is a catalytic agent 32, the membrane covering the sensing layer 18*a* of the enzyme-based electrochemical sensor. The tip 11 is in the subcutaneous space 52 (as seen in FIG. 5) and is consequently bathed in the surrounding biofluid 40. The catalytic agent is dispersed in the membrane by admixing into the membrane solution used in the synthesis of the membrane, a bulk loading procedure, as described in U.S. patent application Ser. No. 10/819,498 of Feldman et al., filed on Apr. 6, 2004.

Insertion Device

An insertion device can be used to subcutaneously insert the sensor into the patient. The insertion device is typically formed using structurally rigid materials, such as metal or rigid plastic. Preferred materials include stainless steel and ABS (acrylonitrile-butadiene-styrene) plastic. In some embodiments, the insertion device is pointed and/or sharp at the tip to facilitate penetration of the skin of the patient. A sharp, thin insertion device may reduce pain felt by the patient upon insertion of the sensor. In other embodiments, the tip of the insertion device has other shapes, including a blunt or flat shape. These embodiments may be particularly useful when the insertion device does not penetrate the skin but rather serves as a structural support for the sensor as the sensor is pushed into the skin.

Sensor Control Unit

The sensor control unit can be integrated in the sensor, part or all of which is subcutaneously implanted or it can be configured to be placed on the skin of a patient. The sensor control unit is optionally formed in a shape that is comfortable to the patient and which may permit concealment, for example, under a patient's clothing. The thigh, leg, upper arm, shoulder, or abdomen are convenient parts of the patient's body for placement of the sensor control unit to maintain concealment. However, the sensor control unit may be positioned on other portions of the patient's body. One embodiment of the sensor control unit has a thin, oval shape to enhance concealment. However, other shapes and sizes may be used.

The particular profile, as well as the height, width, length, weight, and volume of the sensor control unit may vary and depends, at least in part, on the components and associated functions included in the sensor control unit. In general, the sensor control unit includes a housing typically formed as a single integral unit that rests on the skin of the patient. The housing typically contains most or all of the electronic components of the sensor control unit.

The housing of the sensor control unit may be formed using a variety of materials, including, for example, plastic and polymeric materials, particularly rigid thermoplastics and engineering thermoplastics. Suitable materials include, for example, polyvinyl chloride, polyethylene, polypropylene, polystyrene, ABS polymers, and copolymers thereof. The housing of the sensor control unit may be formed using a variety of techniques including, for example, injection molding, compression molding, casting, and other molding methods. Hollow or recessed regions may be formed in the housing of the sensor control unit. The electronic components of the sensor control unit and/or other items, such as a battery or a speaker for an audible alarm, may be placed in the hollow or recessed areas.

The sensor control unit is typically attached to the skin of the patient, for example, by adhering the sensor control unit directly to the skin of the patient with an adhesive provided on at least a portion of the housing of the sensor control unit which contacts the skin or by suturing the sensor control unit to the skin through suture openings in the sensor control unit.

When positioned on the skin of a patient, the sensor and the electronic components within the sensor control unit are coupled via conductive contacts. The one or more working electrodes, counter electrode (or counter/reference electrode), optional reference electrode, and optional temperature probe are attached to individual conductive contacts. For example, the conductive contacts are provided on the interior of the sensor control unit. Other embodiments of the sensor control unit have the conductive contacts disposed on the exterior of the housing. The placement of the conductive contacts is such that they are in contact with the contact pads on the sensor when the sensor is properly positioned within the sensor control unit.

Sensor Control Unit Electronics

The sensor control unit also typically includes at least a portion of the electronic components that operate the sensor and the analyte monitoring device system. The electronic components of the sensor control unit typically include a power supply for operating the sensor control unit and the sensor, a sensor circuit for obtaining signals from and operating the sensor, a measurement circuit that converts sensor signals to a desired format, and a processing circuit that, at minimum, obtains signals from the sensor circuit and/or measurement circuit and provides the signals to an optional transmitter. In some embodiments, the processing circuit may also partially or completely evaluate the signals from the sensor and convey the resulting data to the optional transmitter and/or activate an optional alarm system if the analyte level exceeds a threshold. The processing circuit often includes digital logic circuitry.

The sensor control unit may optionally contain a transmitter for transmitting the sensor signals or processed data from the processing circuit to a receiver/display unit; a data storage unit for temporarily or permanently storing data from the processing circuit; a temperature probe circuit for receiving signals from and operating a temperature probe; a reference voltage generator for providing a reference voltage for comparison with sensor-generated signals; and/or a watchdog circuit that monitors the operation of the electronic components in the sensor control unit.

Moreover, the sensor control unit may also include digital and/or analog components utilizing semiconductor devices, such as transistors. To operate these semiconductor devices, the sensor control unit may include other components including, for example, a bias control generator to correctly bias analog and digital semiconductor devices, an oscillator to provide a clock signal, and a digital logic and timing component to provide timing signals and logic operations for the digital components of the circuit.

As an example of the operation of these components, the sensor circuit and the optional temperature probe circuit provide raw signals from the sensor to the measurement circuit. The measurement circuit converts the raw signals to a desired format, using for example, a current-to-voltage converter, current-to-frequency converter, and/or a binary counter or other indicator that produces a signal proportional to the absolute value of the raw signal. This may be used, for example, to convert the raw signal to a format that can be used by digital logic circuits. The processing circuit may then, optionally, evaluate the data and provide commands to operate the electronics.

Calibration

In general, the calibration is preferably performed by measuring a signal at a particular point in time, meaning by one point calibration, as described in U.S. Pat. No. 5,593,852.

In addition to a transmitter, an optional receiver may be included in the sensor control unit. In some cases, the transmitter is a transceiver, operating as both a transmitter and a receiver. The receiver may be used to receive calibration data for the sensor. The calibration data may be used by the processing circuit to correct signals from the sensor. This calibration data may be transmitted by the receiver/display unit or from some other source such as a control unit in a doctor's office. In addition, the optional receiver may be used to receive a signal from the receiver/display units to direct the transmitter, for example, to change frequencies or frequency bands, to activate or deactivate the optional alarm system and/or to direct the transmitter to transmit at a higher rate.

Calibration data may be obtained in a variety of ways. For instance, the calibration data may simply be factory-determined calibration measurements which can be input into the sensor control unit using the receiver or may alternatively be stored in a calibration data storage unit within the sensor control unit itself (in which case a receiver may not be needed). The calibration data storage unit may be, for example, a readable or readable/writeable memory circuit.

Alternative or additional calibration data may be provided based on tests performed by a doctor or some other professional or by the patient. For example, it is common for diabetic individuals to determine their own blood glucose concentration using commercially available testing kits. The results of this test is input into the sensor control unit either directly, if an appropriate input device (e.g., a keypad, an optical signal receiver, or a port for connection to a keypad or computer) is incorporated in the sensor control unit, or indirectly by inputting the calibration data into the receiver/display unit and transmitting the calibration data to the sensor control unit.

Other methods of independently determining analyte levels may also be used to obtain calibration data. This type of calibration data may supplant or supplement factory-determined calibration values.

In some embodiments of the invention, calibration data may be required at periodic intervals, for example, every eight hours, once a day, or once a week, to confirm that accurate analyte levels are being reported. Calibration may also be required each time a new sensor is implanted or if the sensor exceeds a threshold minimum or maximum value or if the rate of change in the sensor signal exceeds a threshold value. In some cases, it may be necessary to wait a period of time after the implantation of the sensor before calibrating to allow the sensor to achieve equilibrium. In some embodiments, the sensor is calibrated only after it has been inserted. In other embodiments, no calibration of the sensor is needed.

Analyte Monitoring Device

In some embodiments of the invention, the analyte monitoring device includes a sensor control unit and a sensor. In these embodiments, the processing circuit of the sensor control unit is able to determine a level of the analyte and activate an alarm system if the analyte level exceeds a threshold. The sensor control unit, in these embodiments, has an alarm system and may also include a display, such as an LCD or LED display.

A threshold value is exceeded if the datapoint has a value that is beyond the threshold value in a direction indicating a particular condition. For example, a datapoint which correlates to a glucose level of 200 mg/dL exceeds a threshold value for hyperglycemia of 180 mg/dL, because the datapoint indicates that the patient has entered a hyperglycemic state. As another example, a datapoint which correlates to a glucose level of 65 mg/dL exceeds a threshold value for hypoglycemia of 70 mg/dL because the datapoint indicates that the patient is hypoglycemic as defined by the threshold value. However, a datapoint which correlates to a glucose level of 75 mg/dL would not exceed the same threshold value for hypoglycemia because the datapoint does not indicate that particular condition as defined by the chosen threshold value.

An alarm may also be activated if the sensor readings indicate a value that is beyond a measurement range of the sensor. For glucose, the physiologically relevant measurement range is typically about 50 to 250 mg/dL, preferably about 40-300 mg/dL and ideally 30-400 mg/dL, of glucose in the interstitial fluid.

The alarm system may also, or alternatively, be activated when the rate of change or acceleration of the rate of change in analyte level increase or decrease reaches or exceeds a threshold rate or acceleration. For example, in the case of a subcutaneous glucose monitor, the alarm system might be activated if the rate of change in glucose concentration exceeds a threshold value which might indicate that a hyperglycemic or hypoglycemic condition is likely to occur.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Calibration Experiment

Figure 2:
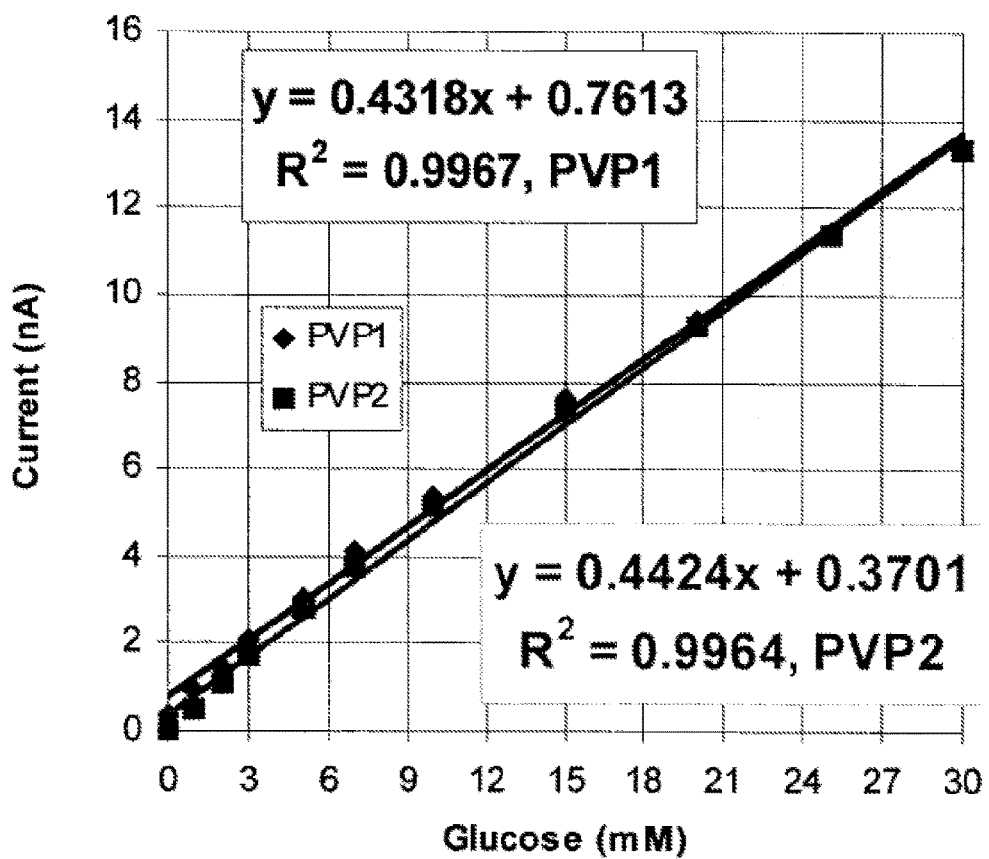
FIG. 2 is a calibration curve for two sensors (PVP1 and PVP2) having diffusion-limiting membranes described herein were tested simultaneously, both at 37° C. The sensors were placed in a PBS-buffered solution (pH 7) and the output current of each of the sensors was measured over various concentrations of glucose (mM).

In a first example, a calibration experiment was conducted in which two sensors (PVP1 and PVP2) having diffusion-limiting membranes described herein were tested simultaneously, both at 37° C. The membranes were prepared from polymers of Formula III above and poly(ethylene glycol) diglycidyl ether (PEGDGE) crosslinkers, having a molecular weight of about 650. In the calibration experiment for each of PVP1 and PVP2, the sensors were placed in a PBS-buffered solution (pH 7) and the output current of each of the sensors was measured over time (FIG. 1) or as the glucose concentration was increased (FIG. 2). The measured output currents (nA) for each of PVP1 and PVP2 was determined and plotted against either time, as shown in the calibration graph of FIG. 1, or glucose concentration (mM), as shown in the calibration graph of FIG. 2.

As shown in FIG. 2, the calibration curve for the two sensors having diffusion-limiting membranes described herein are substantially linear over a relatively large range of glucose concentrations, for example, from zero to about 30 mM, as demonstrated by the best-fit line for the PVP1 sensor (y=0.4318x+0.7613; $R^2$=0.9967) and the PVP2 sensor (y=0.4424x+0.3701; $R^2$=0.9964). This result demonstrates the considerable sensitivity of the membrane-equipped membranes to glucose concentration, at low, medium, and high glucose concentrations, and of particular relevance, at the high end of clinically relevant glucose concentration at about 30 mM.

Example 2

Stability Experiment

In a second example, a stability experiment was conducted in which two sensors having diffusion-limiting membranes were tested, simultaneously, at 37° C. The sensors had membranes prepared from the same polymer and the same crosslinker as those of the sensors described above in the calibration experiment. In this stability experiment, each of the sensors was placed in a PBS-buffered solution (pH 7) at various concentrations of glucose, and the output current of each of the sensors was measured at either room temperature (RT) or used after storage for 1 week at 56° C. (56 C/1 wk). The measured output currents (nA) were plotted against concentrations of glucose (mM), as shown in the stability graph of FIG. 3.

Figure 3:
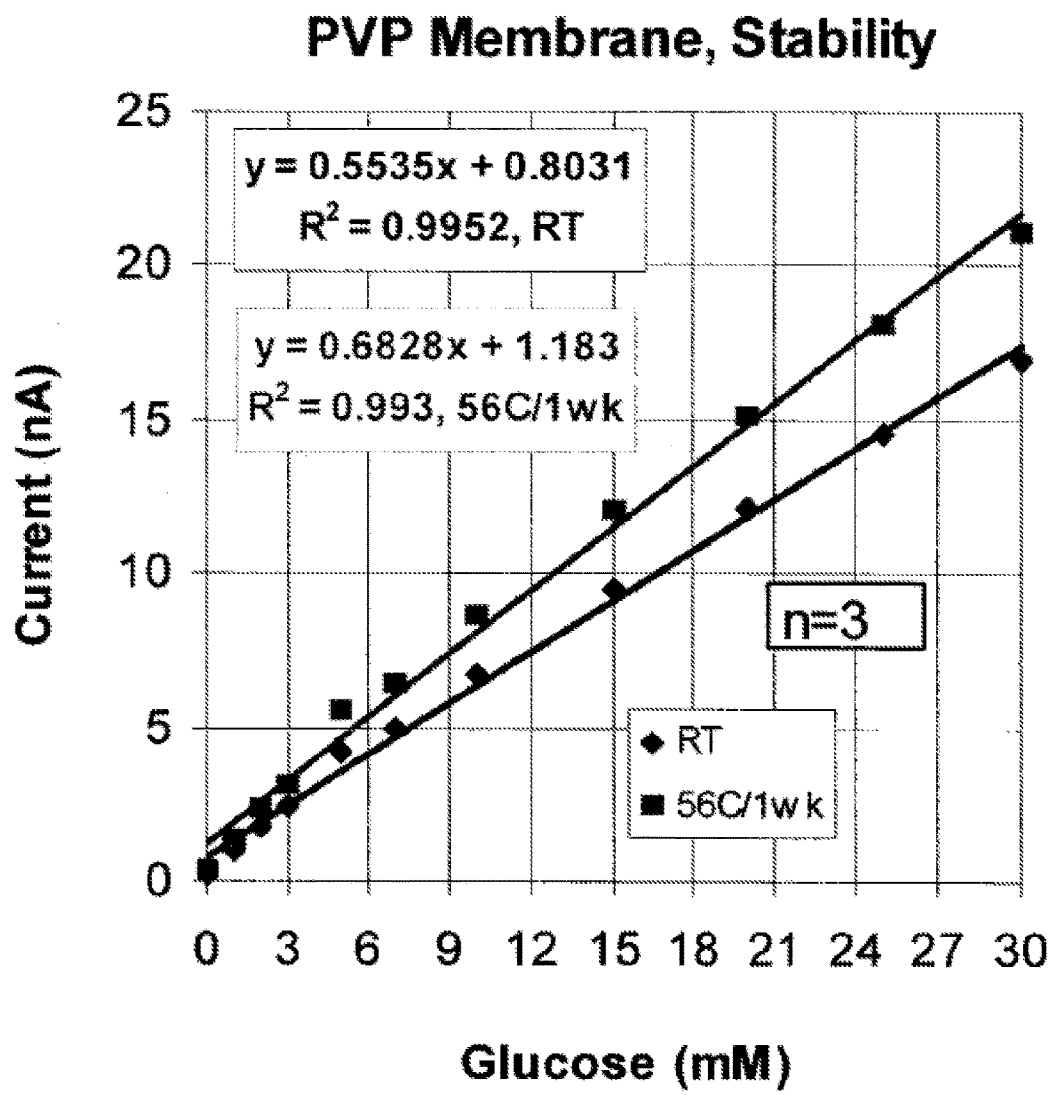
FIG. 3 is a stability curve for two sensors having diffusion-limiting membranes described herein were tested simultaneously. Each of the sensors was placed in a PBS-buffered solution (pH 7) at various concentrations of glucose, and the output current of each of the sensors was measured at either room temperature (RT) or used after storage for 1 week at 56° C. (56 C/1 wk). The measured output currents (nA) were plotted against concentrations of glucose (mM).

As shown in FIG. 3, the stability curve for the two sensors having diffusion-limiting membranes is substantially linear over a relatively large range of glucose concentrations, for example, from zero to about 30 mM, as demonstrated by the best-fit line for the RT sensor (y=0.5535x+0.8031; $R^2$=0.9952) and the 56 C/1 wk sensor (y=0.6828x+1.183; $R^2$=0.993). This result demonstrates the considerable stability and reliability of the membrane-equipped sensors described herein.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A system comprising:
an electrochemical sensor, comprising:
a working electrode comprising:
a sensing layer in contact with a conductive material of the working electrode;
a diffusion limiting membrane layer disposed over the sensing layer, wherein the diffusion limiting membrane layer comprises a crosslinker and a polymer having the formula:

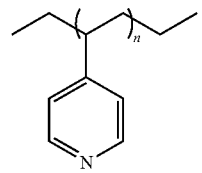

wherein the solid horizontal line represents a polymer backbone and n is an integer from 150 to 15,000; and
a counter electrode in electrochemical communication with the working electrode; and
an electrochemical sensor control unit comprising:
a housing; and
a transmitter for transmitting sensor signals from the electrochemical sensor.

2. The system of claim 1, wherein the sensor control unit further comprises a data storage unit for storing data from the electrochemical sensor.

3. The system of claim 1, wherein the sensor control unit further comprises a reference voltage generator.

4. The system of claim 1, wherein the sensor control unit further comprises a temperature probe.

5. The system of claim 1, wherein the sensing layer of the working electrode comprises a glucose-responsive enzyme.

6. The system of claim 1, wherein the sensing layer of the working electrode comprises a redox mediator.

7. The system of claim 6, wherein the redox mediator comprises a complex selected from the group consisting of a ruthenium-containing complex and an osmium-containing complex.

8. The system of claim 6, wherein the redox mediator is non-leachable with respect to the working electrode.

9. The system of claim 6, wherein the redox mediator is immobilized on the working electrode.

10. The system of claim 1, wherein the crosslinker comprises a poly(ethylene glycol).

11. The system of claim 1, wherein the crosslinker is poly(ethylene glycol) diglycidyl ether.

12. The system of claim 1, wherein the diffusion limiting membrane layer limits flux of glucose or lactate thereacross.

13. The system of claim 1, wherein the diffusion limiting membrane layer limits flux of glucose or lactose thereacross in vivo.

14. The system of claim 1, wherein the analyte responsive enzyme is covalently bound to the polymer.

15. The system of claim 1, wherein the redox mediator is covalently bound to the polymer.

16. The system of claim 1, wherein the analyte responsive enzyme is crosslinked to the polymer.

17. The system of claim 1, wherein the redox mediator is covalently crosslinked to the polymer.

18. The system of claim 1, wherein the diffusion limiting membrane layer is covalently bound to the sensing layer.

* * * * *